US008114081B2

(12) United States Patent
Kohut et al.

(10) Patent No.: US 8,114,081 B2
(45) Date of Patent: Feb. 14, 2012

(54) OSTEOSYNTHESIS PLATE SET

(75) Inventors: Georges Kohut, Spiegel bei Bern (CH); Beat Inauen, Birsfelden (CH); Joanna Norström, Basel (CH); Daniel Andermatt, Möhlin (CH)

(73) Assignee: Synthes USA, LLC, West Chester, PA (US)

( * ) Notice: Subject to any disclaimer, the term of this patent is extended or adjusted under 35 U.S.C. 154(b) by 1317 days.

(21) Appl. No.: 11/437,147

(22) Filed: May 18, 2006

(65) Prior Publication Data
US 2006/0264949 A1    Nov. 23, 2006

Related U.S. Application Data

(63) Continuation of application No. PCT/IB03/05243, filed on Nov. 18, 2003.

(51) Int. Cl.
*A61F 2/30* (2006.01)
(52) U.S. Cl. ............................ 606/71; 606/284; 606/286
(58) Field of Classification Search .................... 606/61, 606/69–73, 76, 77, 280–299
See application file for complete search history.

(56) References Cited

U.S. PATENT DOCUMENTS

| 3,716,050 | A | * | 2/1973 | Johnston | 606/286 |
|---|---|---|---|---|---|
| 4,988,350 | A | * | 1/1991 | Herzberg | 606/65 |
| 5,665,089 | A | * | 9/1997 | Dall et al. | 606/71 |
| 6,096,040 | A | * | 8/2000 | Esser | 606/280 |
| 6,383,186 | B1 | * | 5/2002 | Michelson | 606/70 |
| 7,090,676 | B2 | * | 8/2006 | Huebner et al. | 606/71 |
| 2003/0040749 | A1 | | 2/2003 | Grabowski et al. | |
| 2004/0030339 | A1 | * | 2/2004 | Wack et al. | 606/69 |
| 2004/0102778 | A1 | * | 5/2004 | Huebner et al. | 606/71 |
| 2004/0116930 | A1 | * | 6/2004 | O'Driscoll et al. | 606/69 |
| 2005/0049593 | A1 | * | 3/2005 | Duong et al. | 606/69 |
| 2005/0065524 | A1 | * | 3/2005 | Orbay | 606/69 |

FOREIGN PATENT DOCUMENTS

| FR | 2 472 373 | 7/1981 |
|---|---|---|
| FR | 2 827 500 | 1/2003 |
| GB | 2 245 498 | 1/1992 |

* cited by examiner

*Primary Examiner* — Thomas C. Barrett
*Assistant Examiner* — Christopher Beccia
(74) *Attorney, Agent, or Firm* — Fay Kaplun & Marcin, LLP

(57) ABSTRACT

A set of at least two osteosynthesis plates (2g, 2h) for implantation, anatomical reduction and internal splinting of bone fragments, in particular after fractures of the distal humerus. The two osteosynthesis plates (2g, 2h) according to the invention are provided with drilled holes (3a, 3b, 3c) which are arranged or formed so that the bone crews (12) passing through them come to rest in different directions in space, so that bone screws (12) can pass more completely than in the past through the bone space of the splinted bone (1).

20 Claims, 9 Drawing Sheets

(Prior art)

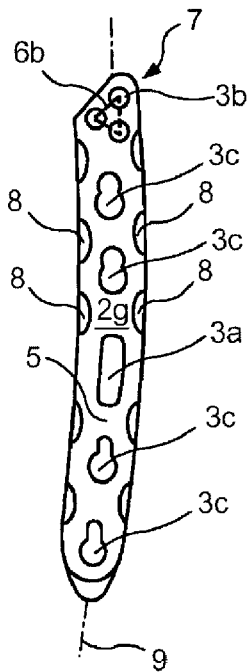
F I G. 8
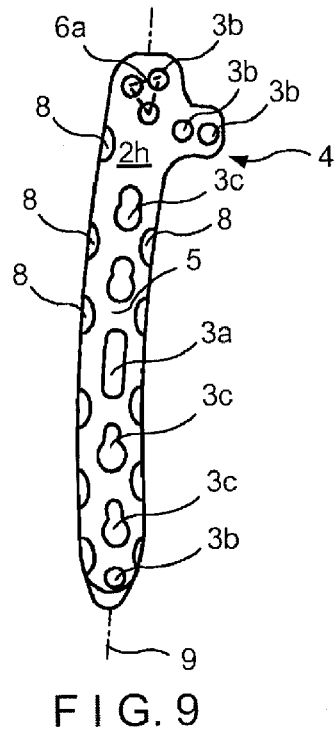
F I G. 9
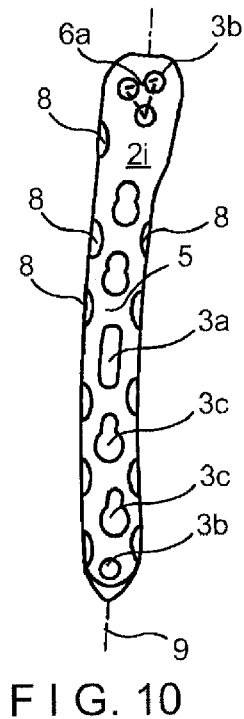
F I G. 10
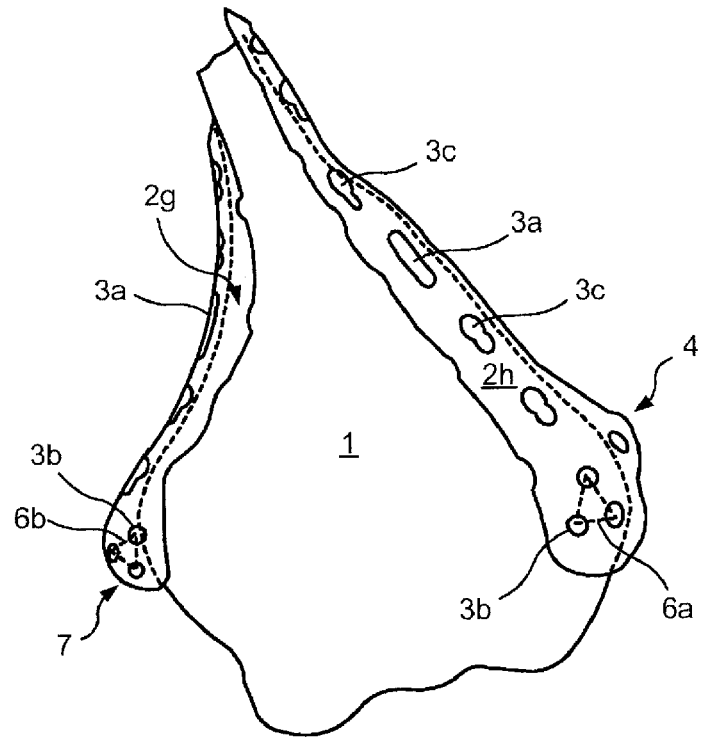
F I G. 11

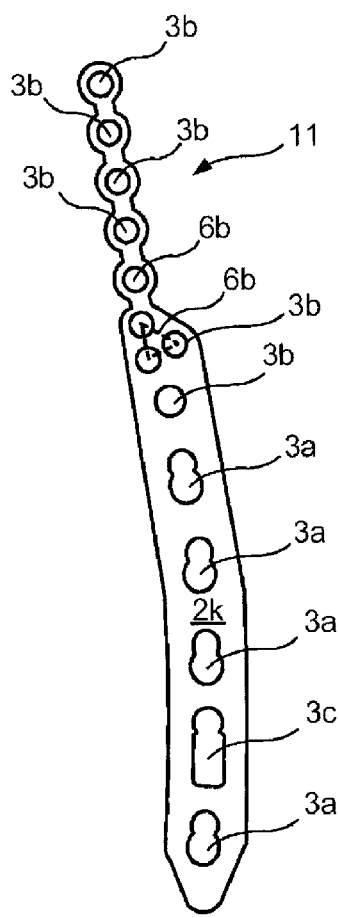
F I G. 16
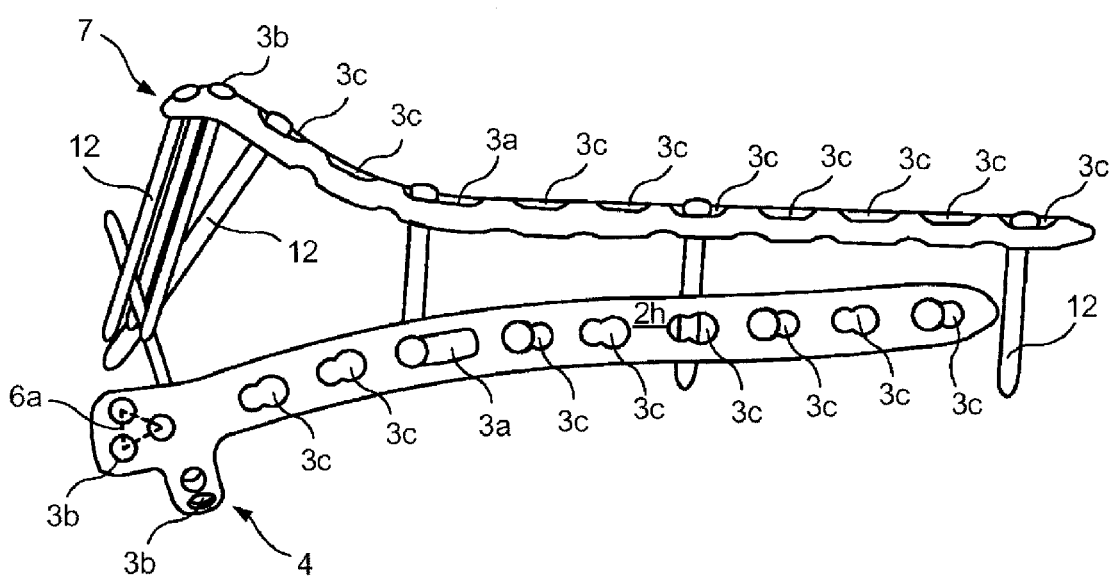
F I G. 17

OSTEOSYNTHESIS PLATE SET

RELATED APPLICATION DATA

The present application is a continuation of the U.S. National Stage designation of co-pending International Patent Application No. PCT/IB2003/05243, filed Nov. 18, 2003, the entire content of which is expressly incorporated herein by reference thereto.

FIELD OF THE INVENTION

The invention relates to an osteosynthesis set comprising at least one first and at least one second osteosynthesis plate having altogether at least four drilled holes for bone screws.

BACKGROUND OF THE INVENTION

Osteosynthesis plates for implantation, anatomical reduction and internal splinting of bone fragments after fractures are widely known. A bone plate for osteosynthesis could be of a general type, which means that the bone plate is not adapted to a certain anatomical position, or it might be of a specific type, which means that the properties of the bone plate have been adapted in order to correspond to a specific type of an anatomical position. For the elbow or distal humerus, the following various solutions have been offered to date (cf. FIGS. 1 to 5):

1) System comprising different plates for an osteosynthesis of a type which is not anatomically specific. These plates were produced for arbitrary anatomical circumstances and may therefore also fit on the distal humerus. These bone plates must be shaped during the operation in order to be adapted to the anatomy of their final anatomical destination, in this case to the shape of the distal humerus;

2) Systems of two osteosynthesis plates cooperating on one bone, one of the plates, the medial or the lateral one, having been anatomically pre-shaped in order to fit the medial or the lateral column of the distal humerus. The other plate is of a type which is not anatomically specific and has to be shaped during the operation in order to fit in its position in the distal humerus;

3) Two-plate systems, one of the plates being pre-shaped in order to fit the anatomy of the lateral arch of the distal humerus, and the other plate being pre-shaped in order to fit the medial ridge of the distal humerus, in positions virtually parallel to one another. These plates require no deformations or only a few deformation during the operation. Bone screws which are introduced through one of the plates come into contact at an obtuse angle with the bone screws which were introduced through the other plate, which is referred to as so-called distal locking of the screws;

4) Two-bone plate systems, one of the bone plates being pre-shaped in order to fit the anatomy of the dorsal aspect of the lateral part, and the other bone plate being pre-shaped in order to fit the medial ridge of the distal humerus and the two plates being fixed on the humerus in positions almost perpendicular to one another. These plates require no deformation or limited deformations during the operation. Bone screws which are introduced through one of the plates come into contact at an acute angle with the bone screws which were introduced through the other plate; and 5) Two-bone plate systems as under 4) above, but, in addition, the plate extends not only distally but also laterally in the most remote distal region of the lateral osteosynthesis plate, said plate having a hole there. Through this hole, a bone screw will come into contact with the bone screws which arrive from the medial plate, at an obtuse angle.

In contrast to other methods, such as simply encasing in plaster, screwing with bone screws or bandaging with wires, osteosynthesis plates have the advantage of fixing a plurality of bone fragments and attaching them in a stable manner to the healthy tissue. In principle, all considerations in the production of osteosynthesis plates were based on the object of forming the shape of these osteosynthesis plates for the implantation on the bone so that anatomically correct positioning and fixing of the osteosynthesis plate without the necessity of changes on the bone and with substantial protection of soft tissue are achieved. The osteosynthesis plates therefore should not be bulky and should have various possibilities for fixing (a plurality of drilled holes).

With the systems obtainable on the market, there are the following disadvantages:

1) Non-specific pre-shaping of the plates requires complicated bending of the plates, which may lead to a loss of mechanical stability of the plate osteosynthesis. Complicated adaptation of the plates is moreover time-consuming. Since the plates are not optimized for the distal humerus, lack of bone support and fixing points for the bone screws may result;

2) For stability reasons, a two-plate system was and is preferred for the distal humerus. With a plate which is shaped to fit a specific anatomical point, and a plate which requires adaptation to its position, the advantage of a system comprising two specially pre-shaped plates is, however, not achieved.

3) A disadvantage of a plate system having a parallel plate configuration is that it requires that all bone fragments lie approximately in a planar, relatively flat space between the two osteosynthesis plates or can be contacted there by inserted bone screws. If, however, bone fragments lie slightly outside this relatively narrow, planar space, they cannot be contacted by the known osteosynthesis plates or by the bone screws in the known osteosynthesis plates and held with reduction. Moreover, the inventors observed that the one-row osteosynthesis plate may have only very little stability to tilting out of the connecting axial plane of the holes. Accordingly, the possibility of loading the bone provided with the plate may therefore be greatly limited.

4) A right-angled plate arrangement ensures stability to tilting but lacks the possibility for screw engagement at an obtuse angle between the bone screw which was introduced through the lateral plate and between the bone screws which were introduced through the medial plate. For very distally located fractures and for fractures in osteoporotic bone, the lack of the meeting of the screw directions at an obtuse angle, the so-called lack of amalgamation via the distal block, will reduce the retention of the bone plates in the bone and hence the stability of the osteosynthesis.

5) A combination of the right-angled plate configuration and a lateral plate form which permits an acute-angled screw engagement between the lateral bone screw which was introduced through the plate and the medial bone screws which were introduced through the plate is ideal for the stability and the retention, but the anatomy of the distal humerus must be followed. The distal part of the plate which is laterally extended must not disturb the soft tissue and the function of the elbow. Systems which are on the market and correspond to this description may disadvantageously come to rest in the region of the points of action of the tendons and thus possibly disturb the function of the elbow. Moreover, the known plates for osteosynthesis do not permit sufficient fixing by the distal block on the medial side.

It is therefore an object of the invention to improve the known sets so that the osteosynthesis plates firstly have better retention on the bone and secondly a larger number of different bone fragments can be reliably repositioned relative to one another. This should take place in a manner which protects soft tissue.

SUMMARY OF THE INVENTION

This object is achieved by the use of a bone plate system comprising at least a first bone plate having upper and lower surfaces and configured and dimensioned for attachment to bone and at least a second bone plate having upper and lower surfaces and configured and dimensioned for attachment to bone. A total of at least four through-holes passing through the first and/or second bone plates from their upper surfaces to their lower surfaces are provided, the at least four holes configured and dimensioned for receiving bone screws in a plurality of different directions. The at least four through holes of the first and second bone plates are configured and dimensioned to accept bone screws in at least four different directions in space. At least one of the two bone plates has at least two holes configured and dimensioned for receiving bone screws substantially parallel to the joint axis, and at least one of the two bone plates has at least one hole which is configured and dimensioned to receive a bone screw substantially perpendicular to the joint axis. The novel formation of the two osteosynthesis plates results in more complete penetration of the bone tissue with bone screws, so that better fixing of the bone fragments can be achieved even with fewer bone screws. Moreover, laterally located bone fragments can also be fixed, and overall substantially more stable and more rotationally rigid splinting is possible.

The idea behind the solution according to the invention lies in the particular division of the bone screws which can be fixed in the osteosynthesis plates with respect to different spatial positions thereof in the mounted state. An osteosynthesis plate set according to the invention therefore makes it possible also to reduce more complicated fractures and in addition to transmit greater forces and moments from the beginning. Premature loosening of the osteosynthesis plates according to the invention is therefore prevented. The preferred formation in which the screws provided are angularly stable supports this effect according to the invention.

The following features produce the following additional effects: By means of a preferred version having altogether more than four drilled holes, for example altogether eight or ten drilled holes, as known per se, further improvements can be achieved if these drilled holes, viewed in two normal planes one on top of the other, with their bore axes facing the bone, make an acute angle with one another in each case, and there is, within the system, an intraoperative retention while these or others make obtuse angles with other bore axes or these bore axes.

In the context of the invention, "make an angle" means not only touching or intersecting bore axes but in particular also bore axes which merely cross, but apparently intersect in the view of intersecting planes. A further improvement of the angle and tilt stability of osteosynthesis plates according to the invention results from the provision of at least two or at least three parallel rows of drilled holes or alternatively at least one row of drilled holes and at least one further drilled hole offset laterally therefrom.

The drilled holes preferably lie along two parallel intersecting planes and additionally at least two further parallel intersecting planes normal to the first ones. Thus, the rotational and tilt stability is improved and moreover better utilization of the bone tissue is possible which tissue tends to be stronger in the edge region than in the middle of the humerus.

Preferably, the bone screws used according to the invention are not fixed only in the bone but also via a thread or partial thread in the holes of the osteosynthesis plate. This advantageously results in improved angle stability of the mounted osteosynthesis plates and reduces the dynamic load of the bone tissue in which the bone screw is anchored.

In addition, this angularly stable design of the osteosynthesis plates according to the invention has the advantage that, even on loosening of one or other bone tissue in the region of one or other bone screw, the other bone screws can guarantee the angular stability of the osteosynthesis plate. By fixing the bone screws in the osteosynthesis plate, the contact pressure of the osteosynthesis plate on the bones is also reduced, which plays a role in helping to avoid pressure-related bone degradation in the tissue region. The embodiments of bone screws and drilled holes known per se can be provided.

Methods in which the bone screws are angle-stabilized by an additional pressure screw inserted only into the osteosynthesis plate are in the view of the inventor preferred in that the osteosynthesis plate must have a relatively great thickness for this purpose and the manipulation with the additional, generally very small, flat screws is difficult under surgery conditions. A particular embodiment of a comparatively small further developed osteosynthesis plate according to the invention is that, in its end region, it has a triangular end region when viewed medially. As a result of this shaping, this osteosynthesis plate can be laid into the outermost distal region of the distal humerus without hindering nerves, tendons or the like there.

In a further developed form, the holes can also be designed so that bone screws can be screwed in and fixed in an angularly stable manner in any desired angular positions. Three drilled holes of at least one osteosynthesis plate preferably serve also for improving the angle stability, but also for improving the tilt stability, the three drilled holes together forming the apices of a preferably equilateral triangle.

A further important, preferred development of osteosynthesis plates lies in the choice of forming at least one of the two osteosynthesis plates, when viewed in the medial direction, in a stem-like manner and with a tab-like part projecting therefrom so that this osteosynthesis plate appears somewhat like a "P" in medial view. Since, according to the invention, both the stem-like and the tab-like parts carry drilled holes, particularly good angle stability is possible as a result of this design, but also particularly good fixing of a very wide range of bone fragments. In addition, this design permits so-called 90° mounting of the two osteosynthesis plates, in which the planes in which the respective bone screws lie are approximately perpendicular to one another, as proposed by AO.

In this embodiment, the bone screw axes of the two osteosynthesis plates intersect at about 90°—compared with the approximately 180° in the case of known systems which protect soft tissue.

In the case of a curvature of the tab-like part, the anatomy of the distal humerus is better taken into account and in addition the possibility of using a very wide range of directions in space for the bone screws is facilitated.

A combination of the osteosynthesis plates with the p-shaped, tab-like part and of the osteosynthesis plates with the triangular, distal region of the osteosynthesis plate has proved to be optimum. Firstly, little material is required and secondly the angle stability is improved or improved penetration of the bone fragments is possible. The two osteosynthesis plates are preferably mounted in such a way that the longer lateral edge of one osteosynthesis plate faces the tab-free lateral edge of the other osteosynthesis plate, so that the tab is on the radial or lateral side and the longer side of the osteosynthesis plate having the triangular section has a longer posterior edge than the length of the anterior edge.

If the holes are formed in a keyhole-like manner, this results in the advantages which have been disclosed in the case of the LCP plate of the Applicant, or, for example, in WO-A-02096309 of the Applicant.

Further developments and details of the invention are disclosed in the description of the figures.

BRIEF DESCRIPTION OF THE DRAWINGS

The figures are described in relation to one another and as a whole. Identical reference numerals denote identical components, and reference numerals with different indices indicate functionally identical components. In the figures.

FIG. 8 shows a schematic diagram of the osteosynthesis plate 2g according to FIGS. 6 and 7 in plan view;

FIG. 9 shows a schematic diagram of the osteosynthesis plate 2h according to FIG. 6 in plan view;

FIG. 10 shows a schematic diagram of the osteosynthesis plates 2i according to FIG. 7 in plan view;

FIG. 11 shows a schematic diagram of the osteosynthesis plates 2g, 2h in the positioned state, rotated somewhat in comparison with FIG. 6;

FIG. 16 shows a medial plate with trochlea support and flexible extension, for adaptation to bones, intraoperatively;

FIG. 17 shows a dorsal view of a plate system comprising medial (without trochlea support) and lateral plate (with flange), right arm;

DETAILED DESCRIPTION OF THE PREFERRED EMBODIMENTS

FIGS. 1-5 show the solutions available today on the market. FIGS. 6, 7, 11 and 12 show osteosynthesis plate sets 2g, 2h, 2i according to the invention in the positioned state.

FIGS. 8-9 show two different osteosynthesis plates 2g, 2h of a set according to the invention, and FIG. 10 shows a variant 2i of the design according to FIG. 9 without a tab.

Figure 3:
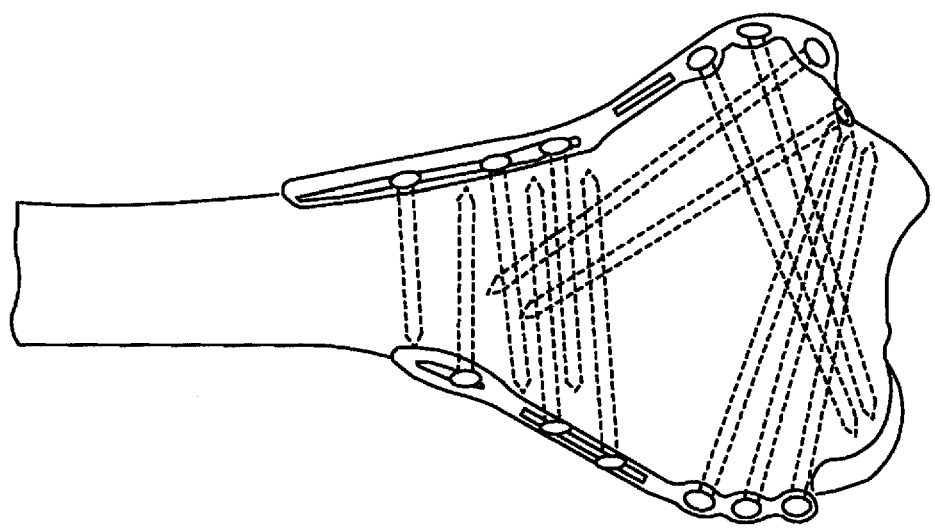
FIG. 3 shows still another prior art plate application with two specific plates mounted 180° relative to one another.
Figure 1:
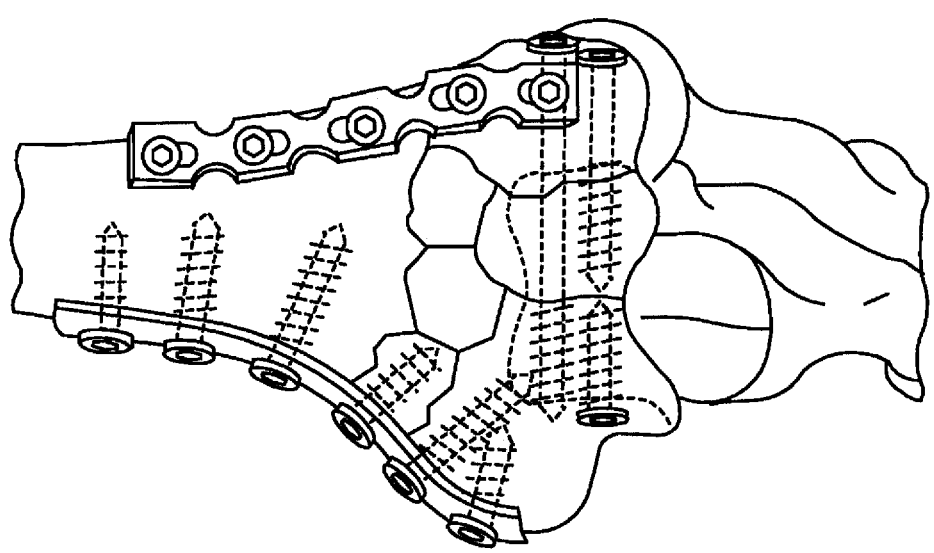
FIG. 1 shows a prior art plate application with non-specific implants.
Figures 2A, 2B, 2C:
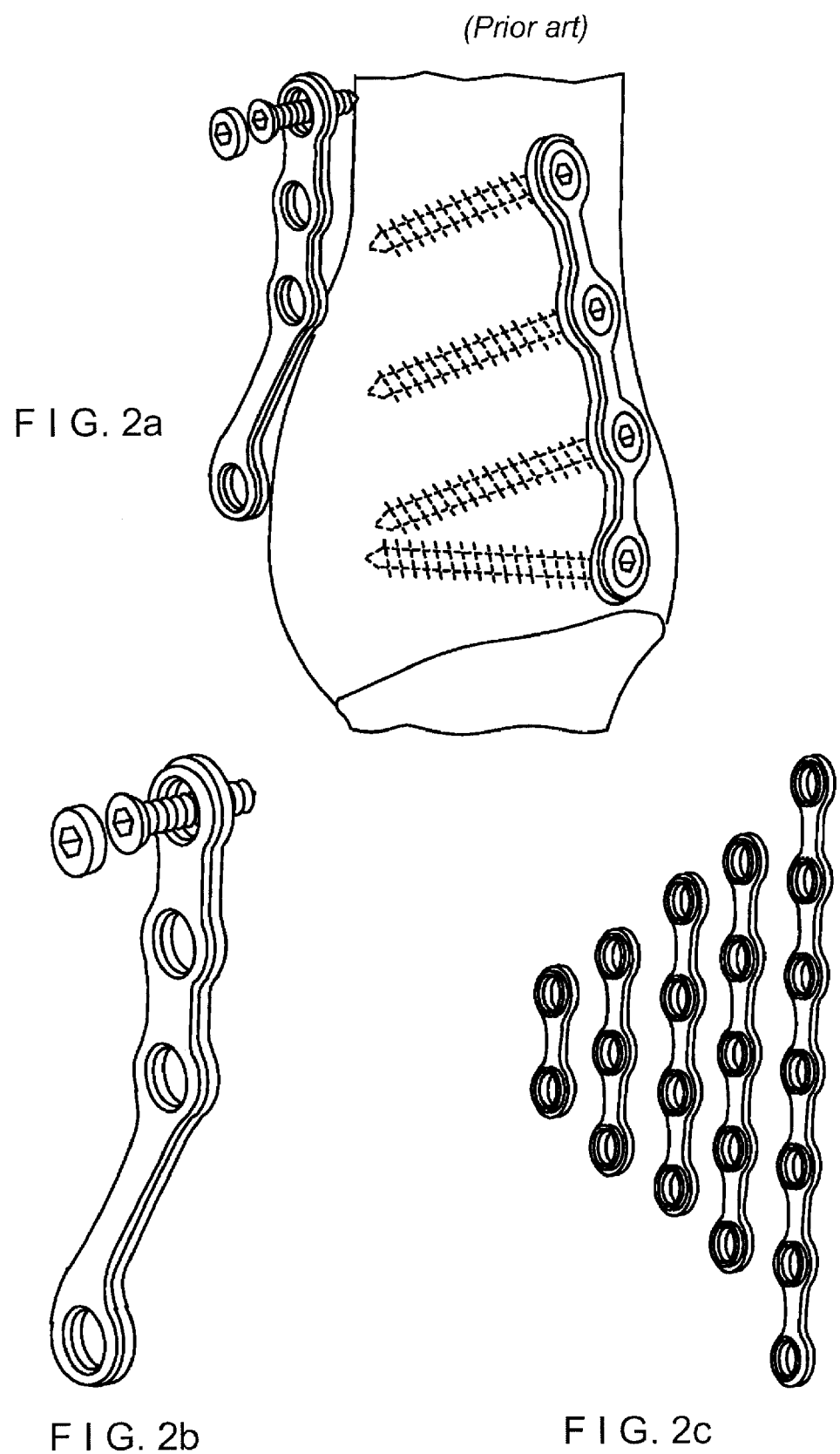
FIGS. 2a-2c show another prior art plate application and system with a specific and a non-specific plate.
Figure 4:
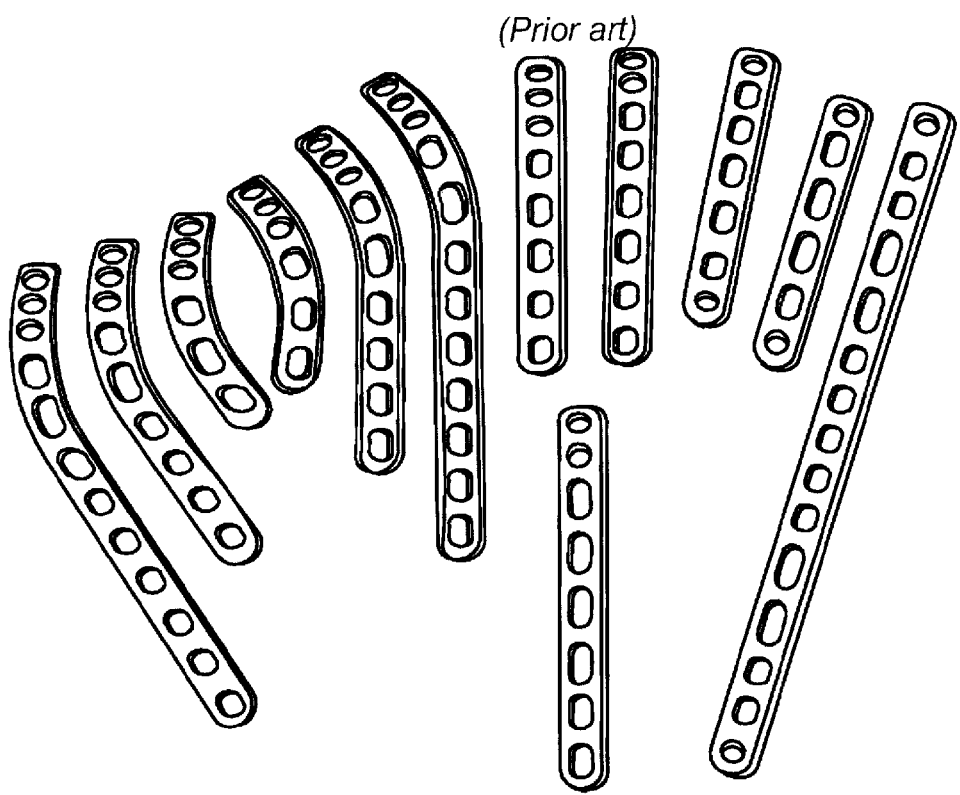
FIG. 4 shows a range of plates from the prior art for osteosynthesis of the distal humerus.
Figure 5:
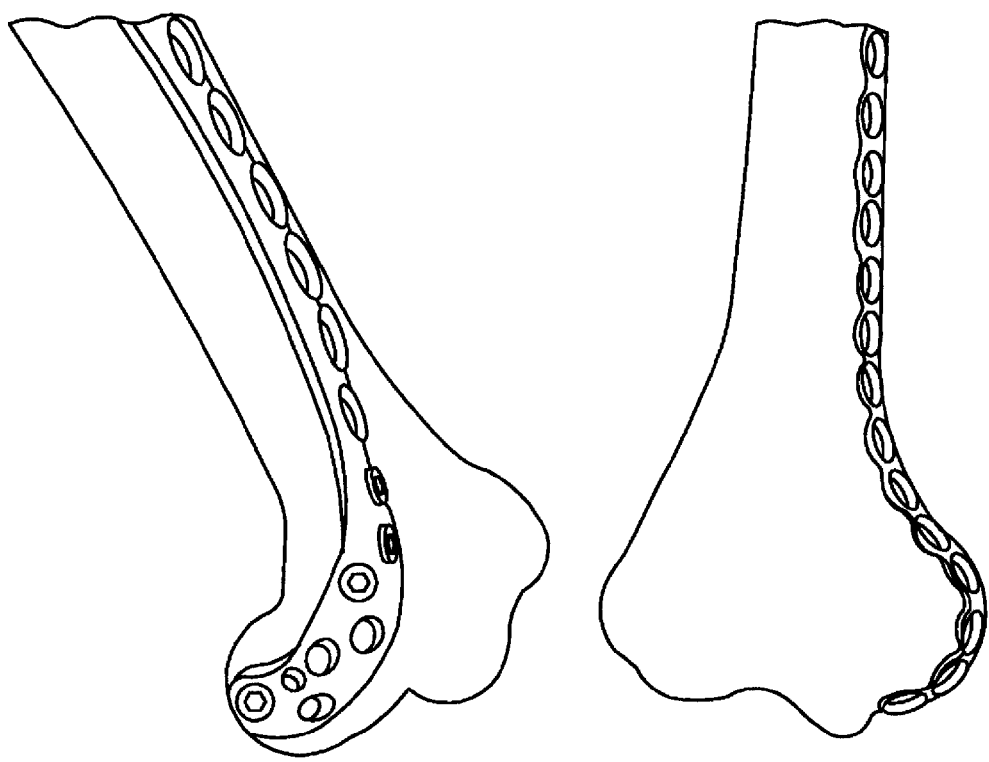
FIG. 5 shows a further prior art plate application with two specific plates 90° to one another and a distal, laterally directed part, showing an obtuse angle of the screws projecting from the 90° plate relative to the screws of the other plate; fixing of the angular position of the screws is not envisaged.
Figure 6:
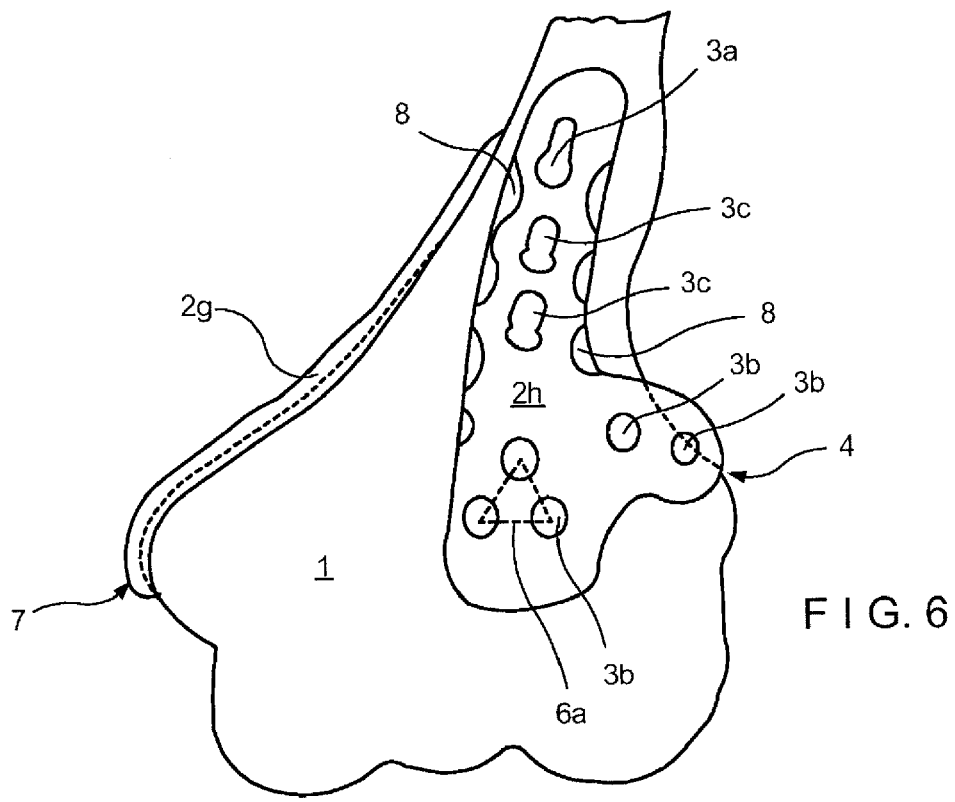
FIG. 6 shows a schematic diagram of the set of osteosynthesis plates 2g, 2h according to a preferred embodiment of the invention in the positioned state; osteosynthesis plate 2h from the set in the positioned state, the osteosynthesis plate 2h having a tab-like part 4 and being curved in a spoon-like manner at the end region.
Figure 7:
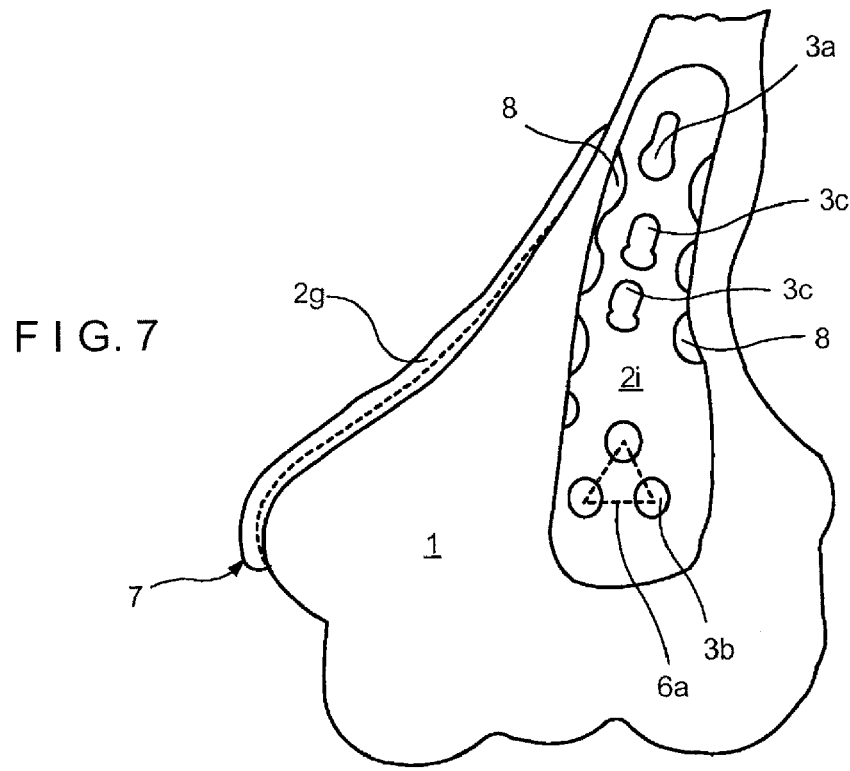
FIG. 7 shows a schematic diagram of another set of osteosynthesis plates 2g, 2i according to another preferred embodiment of the invention in the positioned state.
Figure 12:
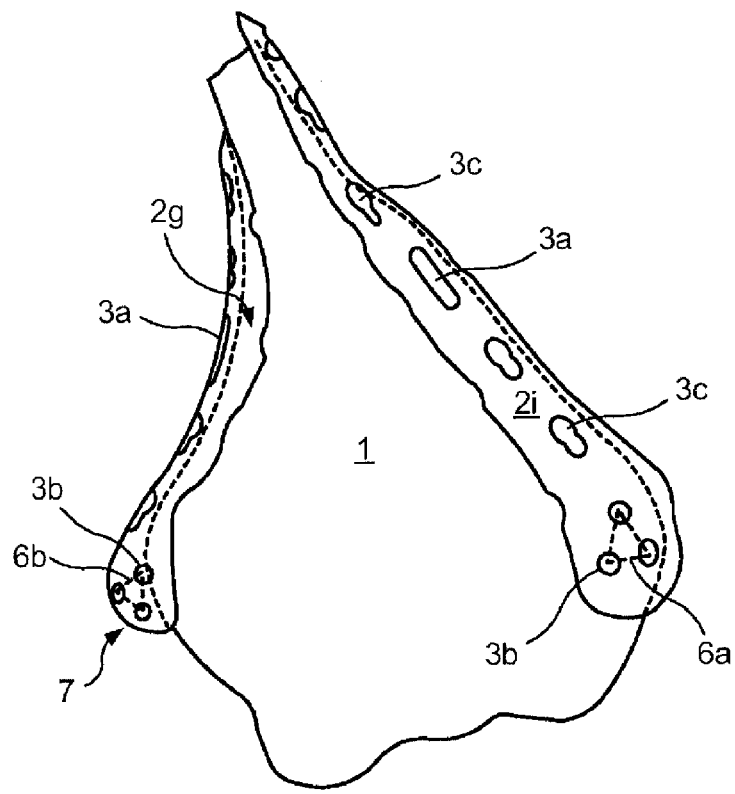
FIG. 12 shows a schematic diagram of the osteosynthesis plates 2g, 2i in the positioned state, rotated somewhat in comparison with FIG. 7.

FIGS. 6 and 7 show various hole shapes 3a, 3b, 3c in the osteosynthesis plates 2h and 2i, and FIGS. 6-7 and 11-12 show the preferred position of the osteosynthesis plates 2g, 2h, 2i on the bone 1.

Figure 18:
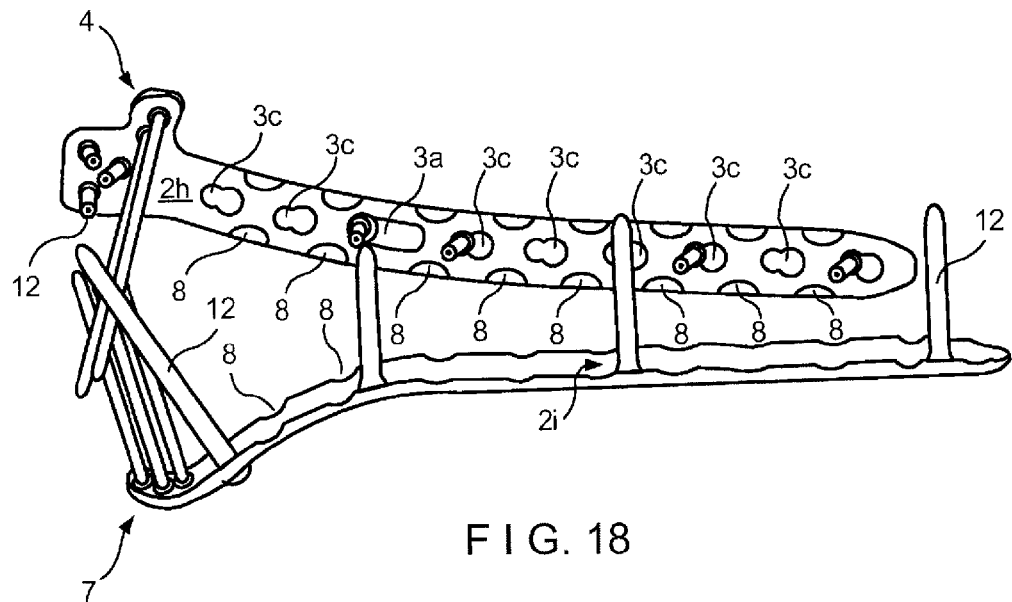
FIG. 18 shows a frontal view of a system according to FIG. 17.
Figure 19:
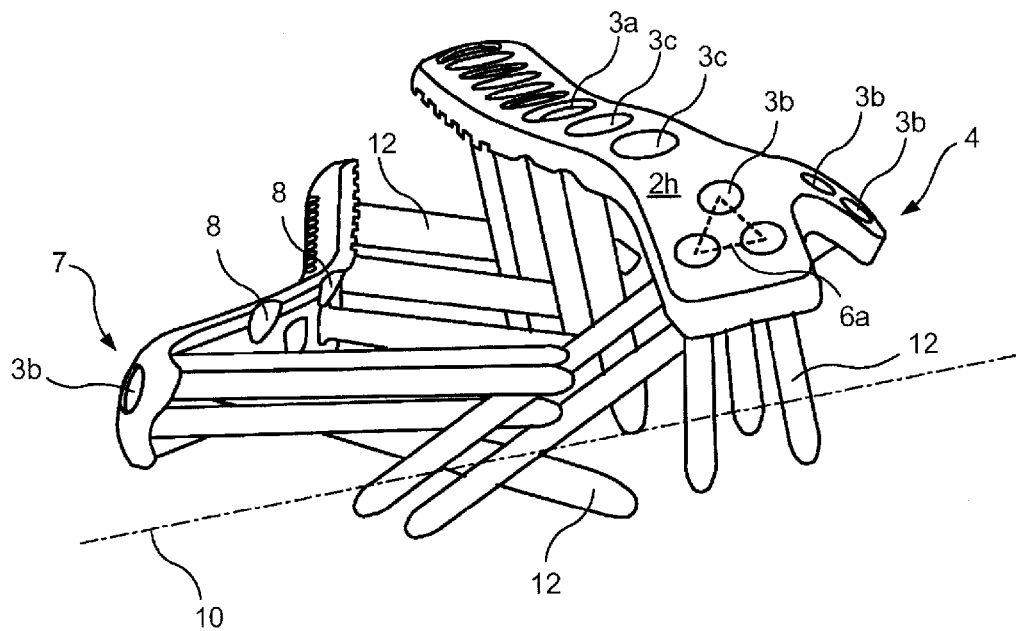
FIG. 19 shows a caudal view of a system according to FIG. 17.

As is evident from the diagrams in FIGS. 6 and 11, drilled holes 3a, 3b, 3c lie along axes which intersect approximately at right angles with comparable axes of the drilled holes 3a, 3b, 3c of the respective other osteosynthesis plate 2h, 2g. In addition, further holes 3b which, owing to the tab-like curvature of the flange 4 are not parallel to the axes of the other holes 3a, 3b, 3c of the same osteosynthesis plate 2h are present in the region of the tab-like part 4. In the conceptual view of a set mounted according to the invention and having bone screws 12 according to FIGS. 17-19, it is evident that these now no longer come to rest only before a narrow, planar region but penetrate the bone space in a very wide range of directions in space at acute and oblique angles relative to one another and are thus most suitable for reducing and for splinting differently positioned bone fragments. In a preferred embodiment, the bone plates may have a thickness in the range of 1.7-2.7 mm, preferably 1.8-2.5 mm. In another embodiment, at least one of the osteosynthesis plates (2g, 2h) has, at least in a partial region, a curvature running transversely to its central axis (9), preferably having a radius of curvature in the range from 18 to 22 mm.

FIGS. 8-10 and, in rudimentary form, FIGS. 6-7 and 11-12 schematically show, in the regions of the osteosynthesis plates 2g, 2h which are free of drilled holes, finger tip-like undercuts 8 which, as shown, are only thinner material parts or are completely eliminated (milled out) regions. These undercuts 8 serve for reducing disturbances of the plate on the bone by minimizing the contact between bone and plate there. In addition the weight of the plate is reduced thereby.

The different shapes of the drilled holes 3a, 3b, 3c own per se, such as slot-like holes 3a, keyhole-like combination holes 3c and round holes 3b, are also evident, at least some of the holes 3a, 3b, 3c according to the invention having an internal thread which cooperates with the bone screws 12 in an angularly stabilizing manner.

Figure 13:
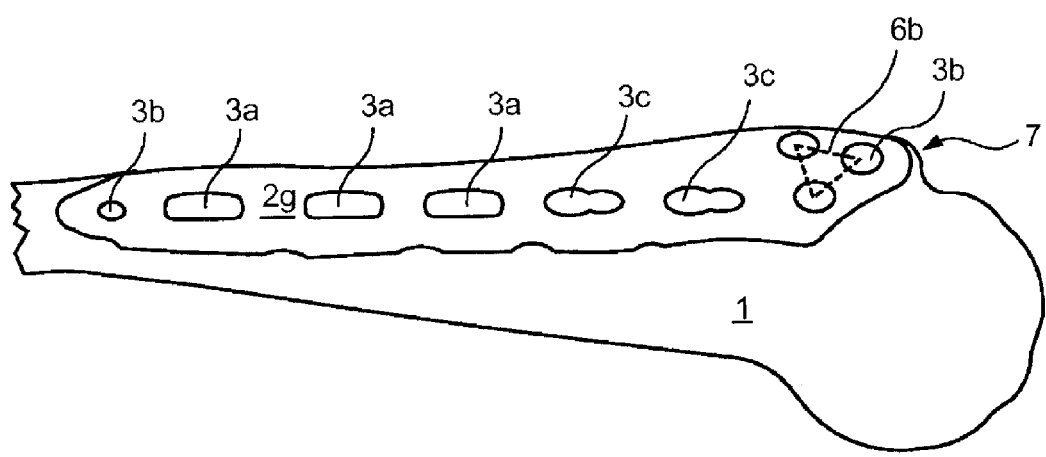
FIG. 13 shows a schematic diagram of a single osteosynthesis plate 2g from the set in the positioned state, the osteosynthesis plate 2g having a triangular end region 7.
Figure 14:
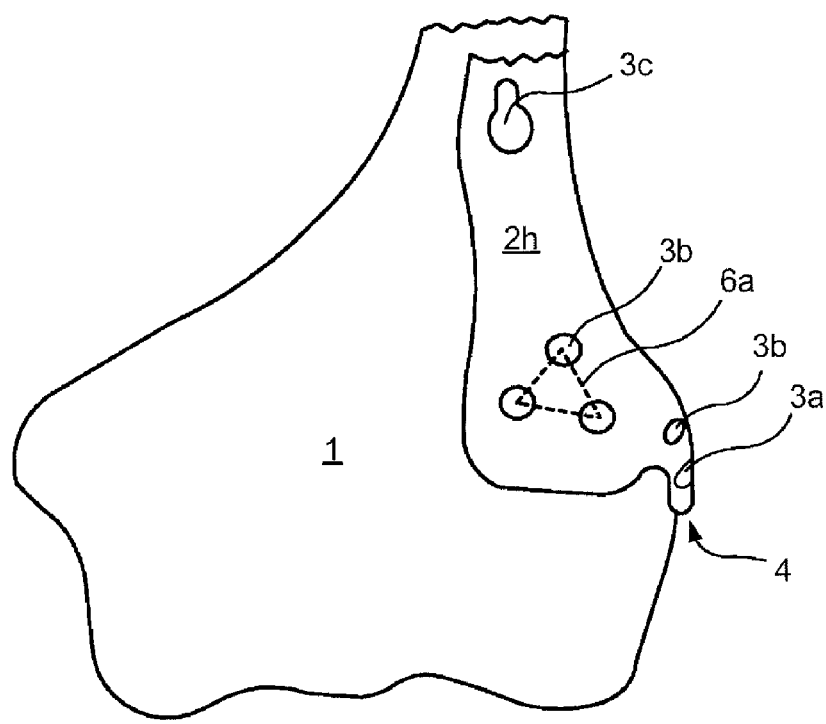
FIG. 14 shows a schematic diagram of a single osteosynthesis plate 2h from the set in the positioned state, the osteosynthesis plate 2h having a tab-like part 4 and being curved in a spoon-like manner at the end region.
Figure 15:
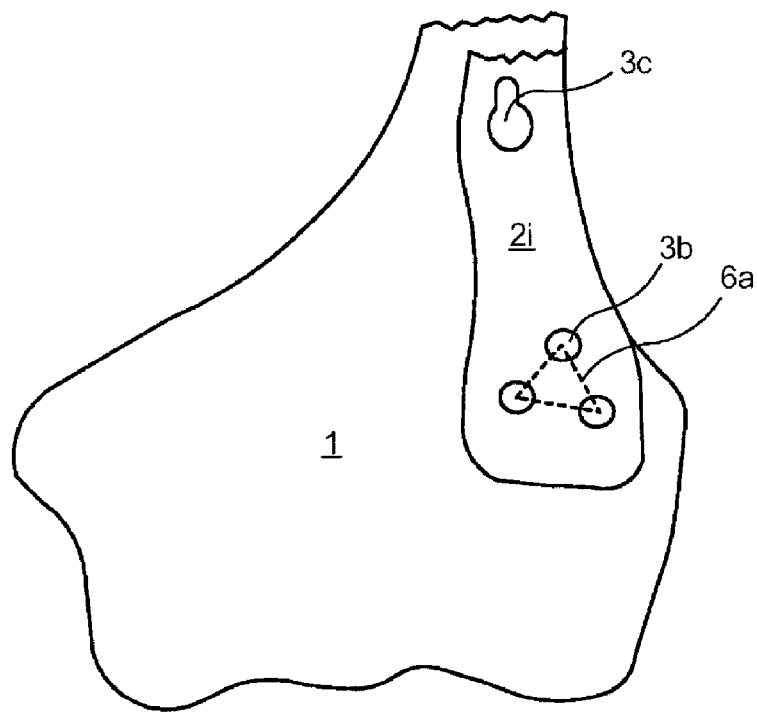
FIG. 15 shows a schematic diagram of a single osteosynthesis plate 2i from the set in the positioned state, the plate having a spoon-like end region.

FIGS. 13-15 each show an osteosynthesis plate 2g, 2h, 2i according to the invention in the positioned state, FIG. 13 showing an osteosynthesis plate 2g having a triangular end region 7, FIG. 14 showing an osteosynthesis plate 2h having a tab-like part 4, which is curved and has a spoon-like end region and FIG. 15 showing an osteosynthesis plate 2i which has a spoon-like end region.

TABLE 1

| List of Reference Numerals | |
| --- | --- |
| 1 | Bone |
| 2g | First osteosynthesis plate |
| 2h | Second osteosynthesis plate |
| 2i | Third osteosynthesis plate |

TABLE 1-continued

List of Reference Numerals

| | |
|---|---|
| 2k | Fourth osteosynthesis plate |
| 3a | Slot-like hole |
| 3b | Round hole |
| 3c | Locking-compression combination hole |
| 3d | Round hole |
| 4 | Tab-like part, flange |
| 5 | Stem-like part |
| 6a | Triangle |
| 6b | Triangle |
| 7 | Triangular end region |
| 8 | Undercuts |
| 9 | Central axis |
| 10 | Joint axis |
| 11 | Narrowed extension |
| 12 | Bone screw |

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed is:

1. A bone plate system treating a bone comprising:
a first bone plate having upper and lower surfaces and configured and dimensioned for attachment to a bone; and
a second bone plate having upper and lower surfaces and configured and dimensioned for attachment to the bone; and
a plurality of through-holes passing through each of the first and second bone plates from their upper surfaces to their lower surfaces, the holes in the first plate being configured and dimensioned to receive bone screws along screw axes non-parallel to one another and the holes in the second plate being configured and dimensioned to receive bone screws along screw axes non-parallel to one another, one of the first and second plates having a plurality of holes configured and dimensioned to receive bone screws which, when the first and second plates are coupled to a bone in desired locations, extend substantially parallel to a joint axis of a joint associated with the bone, the other of the first and second bone plates having a hole configured and dimensioned to receive a bone screw along a screw axis which, when the one of the first and second bone plates is coupled to the bone in the desired location, extends substantially perpendicular to the joint axis,
the first bone plate extending along a longitudinal axis, a first end of the first bone plate being substantially p-shaped with a tab extending from an end portion thereof laterally away from the longitudinal axis and away from the second bone plate, the tab including a tab through-hole configured and dimensioned to receive a bone screw along a screw axis which, when the first and second plates are coupled to the bone in the desired locations, extends substantially parallel to a screw axis of the second bone plate.

2. The system of claim 1, wherein the first bone plate is of a different shape than the second bone plate.

3. The system of claim 1, wherein at least one of the through holes in one of the two bone plates includes a threaded portion to permit angularly stable anchoring of a bone screw having a threaded head.

4. The system of claim 3, wherein the threaded portion of the at least one hole is configured and dimensioned to permit angularly stable locking of a bone screw having a threaded head at a plurality of different angles.

5. The system of claim 1, wherein at least one of the two bone plates has a triangularly-shaped end region in plan view.

6. The system of claim 1, wherein at least three through holes in at least one of the two bone plates form apices of a triangle.

7. The system of claim 6, wherein the triangle is equilateral.

8. The system of claim 1, wherein at least one of the through holes in each of the two bone plates includes a threaded portion to permit angularly stable anchoring of a bone screw having a threaded head.

9. The system of claim 1, wherein at least two of the through holes in at least one of the bone plates have different diameters.

10. The system of claim 1, wherein at least one of the two bone plates includes more than four through holes and each of the four different directions in space forms an acute angle with the joint axis.

11. The system of claim 1, wherein at least one of the two bone plates includes a stem portion and the tab portion projecting therefrom, both the stem portion and the tab portion including at least one through hole.

12. The system of claim 11, wherein the tab portion is curved.

13. The system of claim 1, wherein a distal end of at least one of the two bone plates is curved in a spoon-like manner.

14. The system of claim 1, wherein at least one of the two bone plates has a thickness in the range of about 1.7 to about 2.7 mm.

15. The system of claim 1, wherein at least one of the bone plates has a central axis and a curvature, at least in a partial region, running transversely to its central axis with a radius of curvature in the range from about 18 to about 22 mm.

16. The system of claim 1, wherein at least two through holes in at least one of the bone plates include hole axes that lie in two substantially parallel planes, both of which are non-perpendicular to the upper surface of the bone plate.

17. The system of claim 1, wherein the first bone plate includes the tab and the second bone_plate includes a triangular end region.

18. The system of claim 1, wherein at least one hole has a keyhole shape.

19. The system of claim 1, wherein each bone plate has a thickness, and the thickness of at least one of the bone plates in an area without through holes is less than the thickness of the bone plate in a region with through holes.

20. The system of claim 1, wherein at least one of the two bone plates includes a narrowed extension with at least one hole for a bone screw, and the narrow extension is configured and adapted to be bent around the bone.

* * * * *